(12) United States Patent
Ding et al.

(10) Patent No.: US 7,011,872 B2
(45) Date of Patent: Mar. 14, 2006

(54) METHOD AND PROCESS FOR ENHANCING PROPERTIES AND MEDICAL TUBING PERFORMANCE IN A POLYBUTADIENE MATERIAL

(75) Inventors: Yuan-pang Samuel Ding, Libertyville, IL (US); Birenda K. Lal, Lake Zurich, IL (US); Michael T. K. Ling, Vernoon Hills, IL (US); Richard Mennenoh, McHenry, IL (US); Michael K. Oberhaus, Davenport, IA (US); Lecon Woo, Libertyville, IL (US); Sarah Corbin, Hawthorne Woods, IL (US); George Dillon, Mundelein, IL (US); Dale Pennington, Fox Lake, IL (US); Chuan Qin, Gurnee, IL (US); Patrick T. Ryan, Crystal Lake, IL (US)

(73) Assignee: Baxter International Inc., Deerfield, IL (US)

(*) Notice: Subject to any disclaimer, the term of this patent is extended or adjusted under 35 U.S.C. 154(b) by 258 days.

(21) Appl. No.: 09/939,294

(22) Filed: Aug. 24, 2001

(65) Prior Publication Data

US 2003/0044555 A1 Mar. 6, 2003

(51) Int. Cl.
 *C08L 51/04* (2006.01)

(52) U.S. Cl. ............ 428/35.7; 525/64; 525/89; 525/92 A; 525/98; 525/101; 525/166; 525/176

(58) Field of Classification Search ............... 428/35.7; 525/64, 89, 92 A, 98, 101, 166, 176
See application file for complete search history.

(56) References Cited

U.S. PATENT DOCUMENTS

| | | | | |
|---|---|---|---|---|
| 4,742,137 A | * | 5/1988 | Ono et al. ............... | 526/92 |
| 5,310,497 A | | 5/1994 | Ve Speer et al. | |
| 5,741,452 A | | 4/1998 | Ryan et al. | |

FOREIGN PATENT DOCUMENTS

| | | | |
|---|---|---|---|
| DE | 1234019 B | * | 2/1967 |
| EP | 0 417 552 A2 | | 3/1991 |
| EP | 0 417 552 A3 | | 3/1991 |
| EP | 0 612 799 A1 | | 8/1994 |
| EP | 1 106 190 A1 | | 6/2001 |
| JP | 53075278 A | * | 7/1978 |
| JP | 02305835 A | | 12/1990 |
| JP | 11228957 A | * | 8/1999 |
| WO | 01/56783 A1 | | 8/2001 |

* cited by examiner

*Primary Examiner*—Sandra M. Nolan
(74) *Attorney, Agent, or Firm*—Paula Kelly; Bell, Boyd & Lloyd (57) ABSTRACT

A polymer blend for fabricating medical products having a first 1,2 polybutadiene present from about 1% to about 99% by weight of the blend and having a first melting point temperature; and a second 1,2 polybutadiene present from about 1% to about 99% by weight of the blend and having a second melting point temperature higher than the first melting point temperature.

85 Claims, 4 Drawing Sheets

METHOD AND PROCESS FOR ENHANCING PROPERTIES AND MEDICAL TUBING PERFORMANCE IN A POLYBUTADIENE MATERIAL

RELATED APPLICATIONS

Not Applicable.

CROSS-REFERENCE TO RELATED APPLICATIONS

Not Applicable.

TECHNICAL FIELD

This invention relates to a polyolefin formulation and more particularly to manufacturing medical products from polybutadiene polymers and polymer blends containing polybutadiene. This invention also relates to the treatment of polybutadiene material to enhance property and performance for pump tubing application.

BACKGROUND OF THE INVENTION

In the medical field, where beneficial agents are collected, processed and stored in containers, transported and ultimately delivered through tubes by infusion to patients, there has been a recent trend toward developing materials useful for fabricating such containers and tubing without the disadvantages of currently used materials such as polyvinyl chloride. These new materials for tubings must have a unique combination of properties, so that the tubing may be used in peritoneal dialysis and I.V. administration sets, blood collection and separation devices, blood transfer devices and the like. Among these properties are the materials must be environmentally compatible, have sufficient yield strength and flexibility, have a low quantity of low molecular weight additives, have good dimensional stability and be compatible with medical, pharmaceutical, nutritional and other therapeutic solutions.

It is desirable for medical tubing for many applications to be optically transparent to allow for visual inspection of fluids in the tubing. The optically transparent tubing finds applications, for example, in I.V. administration sets, peritoneal dialysis administration sets and numerous other tubing-containing medical devices where optical clarity is required for whatever reason. Other applications (such as for the delivery of light sensitive compounds and light sensitive fluids) require the tubing to provide visual light and ultraviolet light blockers or filters. The blockers by necessity render the tubing somewhat opaque. For such tubing it is desirable to provide the necessary shielding from visible and UV light while at the same time having sufficient optical clarity to allow viewing an air bubble in fluid flowing through the tubing.

It is also a requirement that the tubing materials be environmentally compatible as a significant quantity of medical tubing is disposed of in landfills and through incineration. Further benefits are realized by using a material that is thermoplastically recyclable so that scrap generated during manufacturing may be incorporated into virgin material and refabricated into other useful articles.

For tubing that is disposed of by incineration, it is necessary to use a material that does not generate or minimizes the formation of by-products such as inorganic acids which may be environmentally harmful, irritating, and corrosive. For example, PVC may generate objectionable amounts of hydrogen chloride (or hydrochloric acid when contacted with water) upon incineration.

To be compatible with medical or dialysis solutions, it is desirable that the tubing material be free from or have a minimal content of low molecular weight additives such as plasticizers, stabilizers and the like. These components could be extracted into the dialysis or therapeutic solutions that come into contact with the material. The additives may react with the solutions or otherwise render the solutions ineffective.

Polyvinyl chloride ("PVC") has been widely used to fabricate medical tubings as it meets most of these requirements. However, because PVC by itself is a rigid polymer, low molecular weight components known as plasticizers must be added to render PVC flexible. As set forth above, these plasticizers may leach out of the tubing and into the fluid passing through the tubing to contaminate the fluid. For this reason, and because of the difficulties encountered in incinerating PVC, there is a need to replace PVC medical tubing.

Polyolefins have been developed which meet many of the requirements of medical containers and tubing, without the disadvantages associated with PVC. Polyolefins typically are compatible with medical applications because they have minimal extractability to the fluids and contents which they contact. Most polyolefins are environmentally sound as they do not generate harmful degradants upon incineration, and in most cases are capable of being thermoplastically recycled. Many polyolefins are cost effective materials that may provide an economic alternative to PVC. However, there are many hurdles to overcome to replace all the favorable attributes of PVC with a polyolefin.

One particular polyolefin of interest is an ethylene and -olefin copolymer obtained using a single-site catalyst such as a metallocene catalyst, a vanadium catalyst or the like. Of this group of copolymers those having a density of less than about 0.915 g/cc are most desirable due to their favorable modulus of elasticity and other physical characteristics. These copolymers obtained using a single site catalyst shall be referred to as ultra-low density polyethylene (m-ULDPE). The m-ULDPE copolymers have better clarity and softness, a low level of extractables and also have fewer additives than traditional polyolefins. This is largely due to m-ULDPE having a narrow molecular weight distribution and a narrow composition distribution. The m-ULDPE is a newly commercialized resin that recently has been used in food and some medical applications. The use of m-ULDPE resins to manufacture medical tubing is the subject of commonly assigned U.S. Pat. No. 5,741,452 which is incorporated herein by reference and made a part hereof.

The '452 Patent does not disclose using a polybutadiene or a blend of various grades of polybutadiene to manufacture flexible components such as medical tubings, and semi-flexible components such as drip chambers. The present inventors have found encouraging results using polybutadienes to manufacture such flexible and semi-flexible components.

Japanese Kokai Patent Application No. Hei 2[1990]-305834 discloses a radiation-resistant polybutadiene composition containing 0.01–2 parts by weight of hindered amine in 100 parts by weight of polybutadiene. This Japanese patent application discloses using syndiotactic 1,2-polybutadiene containing 90% or more of 1,2 bonds as the polybutadiene because it has both softness and strength. The crystallinity is preferably in the range of 15–30%. The Japanese patent application further discloses molding medical devices from polybutadiene and sterilizing by exposing the medical device to radiation. Such medical devices include, for example, tubing, syringes, needle bases for syringe needles, transfusion/blood transfusion sets, blood sampling appliances, and transfusion packs containing the fluid to be transfused. This Japanese patent application does not disclose using blends of polybutadiene resins to form medical products or using solvent bonding techniques to assemble products made therefrom, or using heat treatment to enhance the performance of polybutadiene based medical product such as medical tubing for pump applications.

SUMMARY OF THE INVENTION

A polymer blend for fabricating medical products having a first 1,2 polybutadiene present from about 1% to about 99% by weight of the blend and having a first melting point temperature; and a second 1,2 polybutadiene present from about 1% to about 99% by weight of the blend and having a second melting point temperature higher than the first melting point temperature.

BRIEF DESCRIPTION OF THE DRAWINGS

Other objects, features and advantages will occur to those skilled in the art from the following description and the accompanying drawings, in which.

DETAILED DESCRIPTION OF THE INVENTION

While the invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

The present invention provides non-PVC containing polymers and polymer blends for fabricating medical products such as tubings, drip chambers and the like.

I. Primary Polymers

The polymers of primary interest for fabricating such devices are defined by the 1,2- and 1,4-addition products of 1,3-butadiene (these shall collectively be referred to as polybutadienes). In a more preferred form of the invention the polymer is a 1,2-addition product of 1,3 butadiene (these shall be referred to as 1,2 polybutadienes). In an even more preferred form of the invention the polymer of interest is a syndiotactic 1,2-polybutadiene and even more preferably a low crystallinity, syndiotactic 1,2 polybutadiene. In a preferred form of the invention the low crystallinity, syndiotactic 1,2 polybutadiene will have a crystallinity less than 50%, more preferably less than about 45%, even more preferably less than about 40%, even more preferably the crystallinity will be from about 13% to about 40%, and most preferably from about 15% to about 30%. In a preferred form of the invention the low crystallinity, syndiotactic 1,2 polybutadiene will have a melting point temperature measured in accordance with ASTM D 3418 from about 70° C. to about 120° C. Suitable resins include those sold by JSR (Japan Synthetic Rubber) under the grade designations: JSR RB 810, JSR RB 820, and JSR RB 830.

These JSR polybutadiene grades have the following reported properties set forth in the following table:

| Polybutadiene | 300% Tensile Modulus (psi) | Density (g/cc) | Melting Point (° C.) |
| --- | --- | --- | --- |
| JSR RB 810 | 566 | 0.901 | 71 |
| JSR RB 820 | 886 | 0.906 | 95 |
| JSR RB 830 | 1130 | 0.909 | 105 |

II. Blends Containing Primary Polymers

The present invention provides multiple component polymer blends including the polybutadiene resins set forth above. In a preferred form of the invention, the polybutadiene resins will constitute at least 50% by weight of the blend. One particularly suitable polymer blend includes a first low-crystallinity syndiotactic 1,2 polybutadiene having a first melting point temperature and a second low-crystallinity syndiotactic 1,2 polybutadiene having a second melting point temperature lower than the first melting point temperature. In a preferred form of the invention, the first melting point temperature will be higher than about 90° C. Also, in a preferred form of the invention, the first melting point temperature will be lower than about 120° C. and even more preferably lower than about 110° C. and even more preferably lower than about 105° C. In an even more preferred form of the invention, the first melting point temperature will be higher than about 90° C. and more preferably from about 91° C. to about 120° C. In a preferred form of the invention, the second melting point temperature will be lower than 91° C.

Also in a preferred form of the invention, the two-component polymer blend, the first low-crystallinity syndiotactic 1,2 polybutadiene will be present by weight of the blend from about 1% to about 99%, more preferably from about 40% to about 70% and even more preferably from about 45% to about 65% while the second low-crystallinity syndiotactic 1,2 polybutadiene will be present by weight of the blend from about 99% to about 1%, even more preferably from about 30% to about 60% and even more preferably from about 35% to about 55%.

Of course the present invention contemplates adding additional components to the two-component blend and in a preferred form of the invention the additional components will be selected from polyolefins. What is meant by the term "polyolefin" is polymers obtained through polymerizing an olefin. What is meant by the term "olefin" is any unsaturated hydrocarbons containing one or more pairs of carbon atoms linked by a double bond. Olefins are meant to include: (1) cyclic and acyclic (aliphatic) olefins wherein the double bond is located between carbon atoms forming part of a cyclic (closed-ring) or of an open-chain grouping, respectively, and (2) monoolefins, diolefins, triolefins etc., in which the number of double bonds per molecule is, respectively, one, two, three or some other number. Polyolefins include homopolymers and copolymers. Polyolefins include, to name a few, polyethylene, polypropylene, polybutene, polybutadiene (especially the low-crystallinity syndiotactic 1,2 polybutadienes described above), norbornene/ethylene copolymers and the like.

It is also contemplated that additional processing aids can be added. In particular, it is desirable to add from about 1% to about 5% by weight of a preservative and more preferably a preservative selected from hindered amines. Such hindered amines are identified in *Plastics Additives and Modifiers Handbook,* which is incorporated in its entirety herein by reference and made a part hereof. One particularly suitable hindered amine is sold by Ciba Geigy under the tradename Tinuvin 770.

In preferred form of the invention the components of the blends will have refractive indicies that differ by equal to or less than about 0.08, more preferably equal to or less than about 0.04 and most preferably equal to or less than about 0.01. Also, in a preferred form of the invention, the components of the blends will have a difference in their densities of equal to or less than about 0.008 g/cc, more preferably equal to or less than about 0.004 g/cc and most preferably equal to or less than about 0.002 g/cc.

IV. Blending of Components of Polymer Blends

The blends of the present invention can be provided individually and blended by tumble blending or using standard Banburry type mixers, twin screw type mixers, or a single screw type mixer. It is also contemplated that the desired components can be blended, extruded and pellitized. It is also contemplated to prepare the desired blend of resins using series of reactors connected in sequence.

In a preferred form of the invention for the latter described process, there is a reactor provided for each of the polymers in the blend. Monomers and catalyst are added into the first reactor. The reaction conditions, particularly pressure, temperature, and residence time, are controlled so that the amount of product produced in each reactor is within certain limits and the product has certain properties. The catalyst used in each reactor is a single-site catalyst or a blend of single-site catalysts or a blend of single-site catalyst with other types of catalysts.

In a first reaction step, monomers and catalyst are added into the first reactor. The reaction conditions, particularly pressure, temperature, and residence time, are controlled in the first reactor. The reacted and unreacted components from the first reactor are transported to the second reactor. As with the first reactor the conditions in the reactor are controlled to produce the desired grade of resin. The reacted and unreacted components from the second reactor are transported to the third reactor to produce a third grade.

The use of multistage processes for polymerization to produce blends of resins of different molecular weights is well known. For example, U.S. Pat. No. 4,336,352, which is incorporated herein by reference, discloses polyethylene compositions consisting of three different polyethylenes. The present invention contemplates using two or more reactors in series to prepare blends of more than one type of polybutadiene or to mix polybutadiene with other polyolefins and particularly polyethylene. In one preferred form of the invention, a series of two reactors are utilized. In the first stage polybutadiene having a density between 0.905–0.915 g/cc is polymerized and the proportion of this fraction to the end product is 1–50%. In the next polymerization stage polybutadiene having a density between 0.904–0.895 g/cc is produced and the proportion of this fraction to the end product is 1–50%. It is contemplated that additional stages could be added to this process or substituted for one of the first two stages to add ethylene.

V. Radiation Exposure

In a preferred form of the invention the polymer blends and products made therefrom (discussed below) are exposed to a sterilization dosage of radiation. Acceptable radiation treatments include, for example, exposing the blend or product to electron beam radiation or gamma radiation. Sterilization radiation is typically carried out at much lower doses of radiation than are used to cross-link polymers. The typical magnitude of such sterilization radiation is on the order of about 25 kGys, but can sometimes be as low as 15 kGys.

In some instances, although not necessarily, exposing the blend or product made therefrom to radiation sterilization results in a measurable change in gel content of the blend or product. Gel content indicates the percentage of the weight of insolubles to the weight of the blend or product. This definition is based on the well-accepted principle that crosslinked polymer materials are not dissolvable.

For polybutadiene material, a gel content above 20%, more preferably greater than about 40%, or any range or combination of ranges therein, may increase the mechanical strength and prolong the time of service in the medical pump tubing application.

VI. Heat Treatments to Enhance Tubing Performance

In this invention, we has discovered that proper heat treatment will have the effect of beneficially enhancing the performance of polybutadiene material for medical applications, especially for medical pump tubing applications. A monolayer or a multilayer tubing made of a single or a blend of two or more low crystallinity syndiotactic 1,2 polybutadiene resins can be heat treated to enhance its performance for pump tubing applications.

For pump tubing applications, it is desirable for the tubing material to display minimal changes in physical properties over time, to have a low and stable elastic modulus, and to be strong in tensile properties. For semicrystalline materials, such as polyethylene and polypropylene, the elastic modulus usually increases with time after the tubing extrusion. Heat treatment of these tubings will usually increase the crystallinity as well as the elastic modulus, rendering the tubing too stiff for pump applications.

In the present invention, we have discovered that we can formulate the pump tubing from syndiotacatic, 1,2 polybudiene materials with a relatively high elastic modulus to take the benefit of higher mechanical strength. After extruding the formulation into tubing, the elastic modulus will increase over time as its crystallinity increases over time, rendering the tubing less and less suitable for pump application. However, we have discovered that, by applying a carefully controlled heat treatment to the tubing after extrusion, the tubing is stabilized to minimize or stop the change of the elastic modulus over time, even though the crystallinity of the material may still continue to increase over time after the heat treatment.

Very surprising, after this controlled heat treatment, the elastic modulus drops to a stable and desired level. More surprisingly, even when the tubing material has been stiffened to a different level over time after the extrusion, the controlled heat treatment can reduce the elastic modulus to the stable level, where it remains. The ability to lower and stabilize the elastic modulus of an initially stiff and strong tubing material will be beneficial for pump tubing application as the enhanced durability and elasticity of a stiffer tubing is not lost with a reduction in the elasticity. Most surprisingly, after the heat treatment, the tensile property of the 1,2 polybutadiene material is fundamentally changed. The material before treatment has a distinct tensile yield point as is apparent in the kink point on a stress-strain curve. After the treatment, the tensile curve becomes a smooth curve without a distinct yield point as a kink on the stress-strain curve. The tensile curve of the heat treated curve behaves similar to a flexible plasticized polyvinyl chloride material.

The heat treatment process includes the steps of exposing the tubing to heat from about 45° C. to about 95° C. and more preferably from about 50° C. to about 90° C. and most preferably 60° C. to about 90° C. The heat, in a preferred form of the invention, is provided by an oven, and more preferably in a reduced oxygen concentration environment. The tubing should be placed in the oven from about 2 minutes to about 360 minutes or beyond depending upon the temperature of the oven and the amount of stabilizer levels in the material formulation. The data in the examples show that tubing made from one of the polybutadienes set forth above has a tendency over time to increase in modulus of elasticity (day 3=2900 psi, day 31 and beyond in excess of 4900 psi) (see Example 2). Tubing from the same material if subjected to a heat treatment process having various initial moduli of elasticity (from 2900 psi to 5000 psi) results in tubings having substantially the same modulus of elasticity (from 1850 psi to 2210 psi) (see Example 3). Further, the tubing after heat treatment has a lower modulus of elasticity, which is desirable for tubing used with pumps, and maintains this reduced modulus of elasticity over time. Thus, the tendency of the non-heat treated tubing to increase in modulus of elasticity is reduced or almost completely eliminated.

Examples 4 and 5 below show that there can be a broad heat treatment window in terms of temperature of the oven and the time in the oven to achieve desirable results. Examples 4 and 5 also show that this heat treatment stabilizing effect is present regardless of whether the tubing has been sterilized with gamma radiation. The gamma irradiated tubings show a slightly increased modulus of elasticity over the corresponding non-irradiated tubings; however, both non-irradiated and irradiated tubings show a stable modulus of elasticity over time.

VII. Medical Devices

Figure 3:
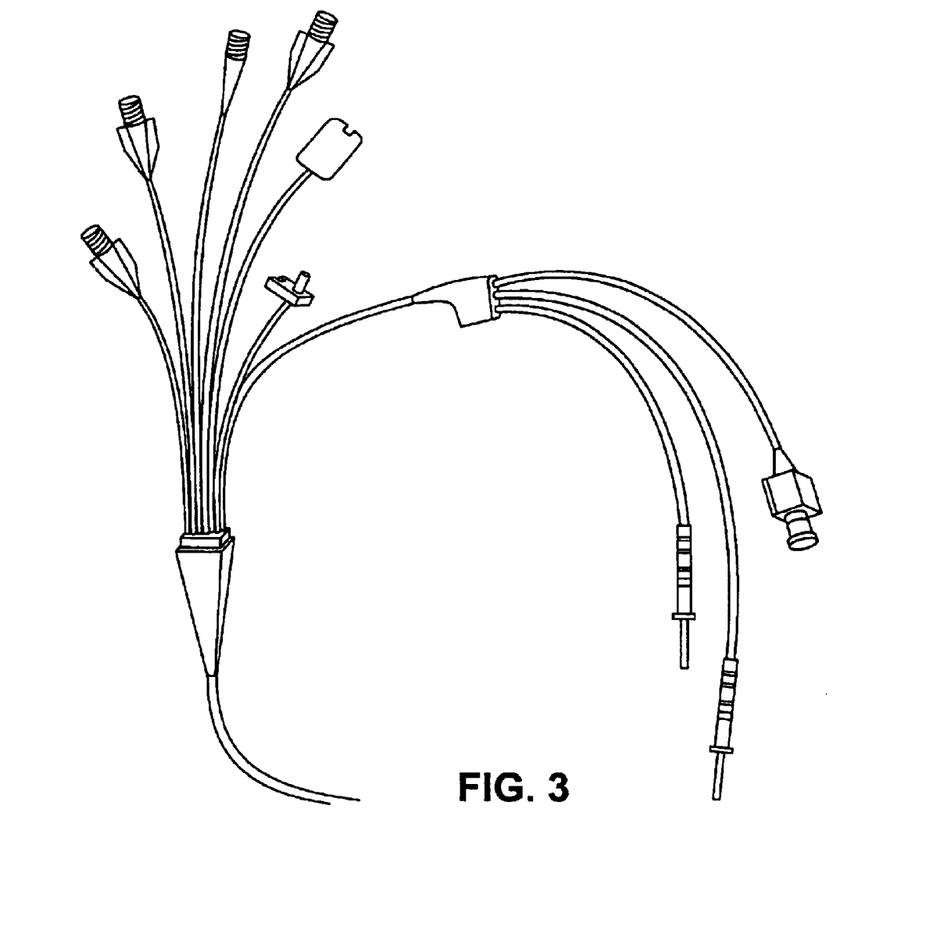
FIG. 3 is a plan view of a dual lumen tubing.
Figure 4:
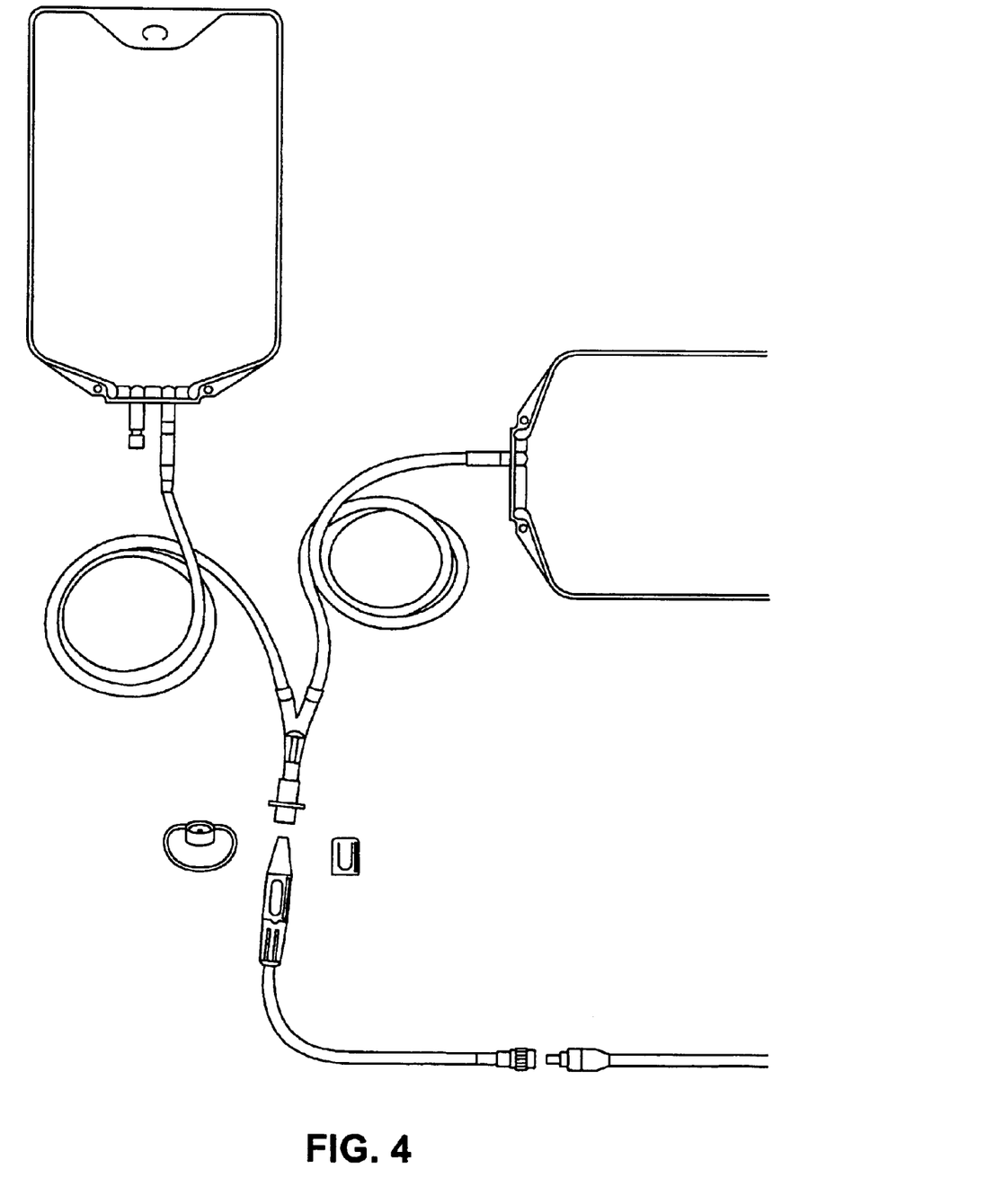
FIG. 4 is a plan view of a peritoneal dialysis administration set.
Figure 5:
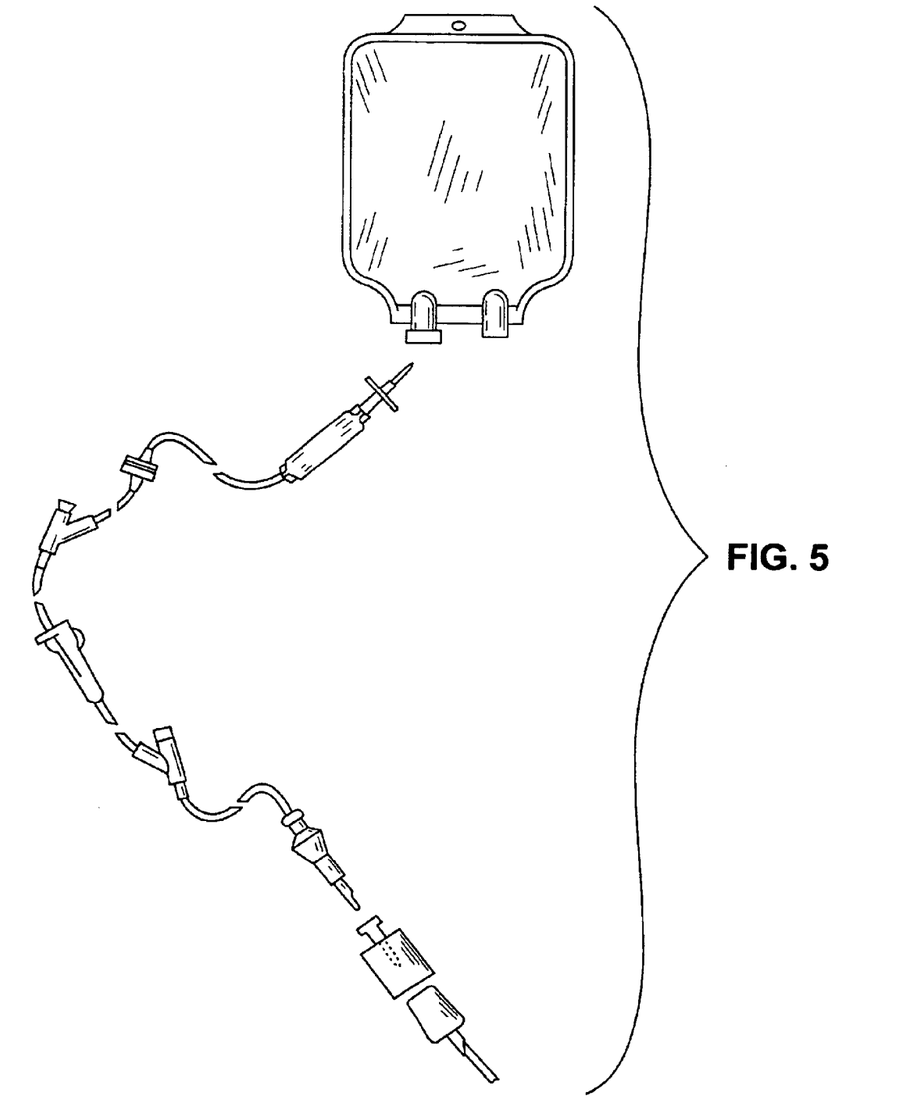
FIG. 5 is a plan view of a I.V. administration set.
Figure 6:
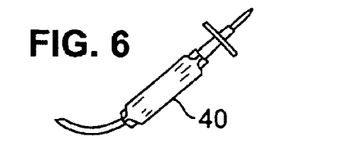
FIG. 6 is a plan view of a drip chamber.

The primary polymers individually and blends containing the same are capable of being fabricated into monolayer tubings (FIG. 1), multiple layered tubings (FIG. 2), a dual lumen tubing (FIG. 3), peritoneal dialysis administration set (FIG. 4), an I.V. administration set (FIG. 5) and a drip chamber (FIG. 6).

A. Tubings

The tubings of the present invention shall have the following physical properties: a modulus of elasticity of less than about 20,000 psi, more preferably less than about 10,000 and most preferably less than about 5,000 psi, an internal haze of less than about 25% when measured in accordance with ASTM D1003, is capable of being fabricated at a throughput rate of greater than about 100 ft/min, more preferably greater than about 200 ft/min, even more preferably greater than about 250 ft/min and most preferably equal to or greater than about 300 ft/min; a yield strength of from about 400 psi to about 1500 psi and more preferably from about 600 psi to about 800 psi, and the tensile curve around the yield curve should be smooth (as shown in Example 6), is capable of being repeatedly used with a medical tubing clamp with an occlusion force typically of about 5 lbs without significantly damaging the tubing and is capable of solvent bonding to a rigid component.

Figure 1:
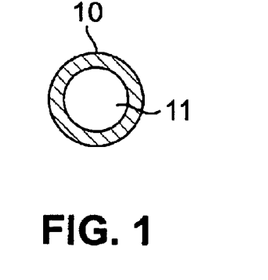
FIG. 1 is a cross-sectional view of a monolayer tubing.

The monolayer tubing 10 shown in FIG. 1 has a sidewall 11 made from one of the multiple component polymer blends described above. In a preferred form of the invention the tubing from the blend is exposed to radiation in accordance with the processes described above.

Figure 2:
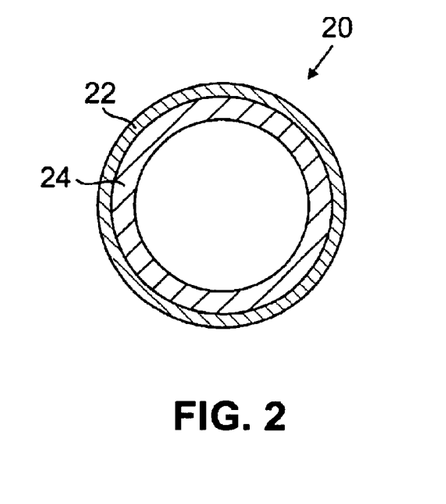
FIG. 2 is a cross-sectional view of a multiple layered tubing.

The multiple layered tubing 20 shown in FIG. 2 will preferably have two layers, concentrically mounted with respect to one another, but could have additional layers without departing from the scope of the present invention. In a preferred form of the invention, the multiple layered tubing 20 will have a first layer 22 and a second layer 24. At least one of the first layer 22 or the second layer 24 will have at least 50% of one of the 1,2 polybutadienes set forth above. In one embodiment of the present invention either the first layer 12 or the second layer 14 will contain at least 50% of one of the 1,2 polybutadienes set forth above and the other layer will be a polyolefin.

In a more preferred form of the invention each of the first layer 22 and the second layer 24 will have at least 50% of one of the 1,2 polybutadienes set forth above. One such embodiment includes the first layer 22 being of a first low-crystallinity syndiotactic 1,2 polybutadiene and the second layer 24 being of a second low-crystallinity syndiotactic 1,2 polybutadiene. The first and second low-crystallinity syndiotactic 1,2 polybutadienes can be the same grade, different grades, or a blend of polybutadienes.

In an even more preferred form of the invention, one of the first layer 22 or the second layer 24 will be a two-component blend of low-crystallinity syndiotactic 1,2 polybutadienes. The other layer can be a polyolefin, a single low-crystallinity syndiotactic 1,2 polybutadiene, or a blend containing at least 50% of a low-crystallinity syndiotactic 1,2 polybutadiene. The first layer 12 and the second layer 14 can be selected from single polymers selected from the 1,2 polybutadienes set forth above, or the polybutadiene containing blends set forth above.

In one preferred form of the invention the first layer 22 (outer) will be a low-crystallinity syndiotactic 1,2 polybutadiene having a melting point temperature higher than about 90° C., or is a two-component blend containing a first low-crystallinity syndiotactic 1,2 polybutadiene having a melting point higher than about 90° C. (more preferably from about 91° C. to about 120° C.) and a second low-crystallinity syndiotactic 1,2 polybutadiene having a melting point lower than about 90° C. The second layer 24 (inner) will be of a blend of a low-crystallinity syndiotactic 1,2 polybutadiene having a melting point higher than about 90° C. and a low-crystallinity syndiotactic 1,2 polybutadiene having a melting point lower than about 90° C. The relative amounts of the components within these blends are set forth above in Section II.

B. Pump Compatible Tubings

For tubings that are to be used with infusion pumps, especially those pumps that apply energy to a sidewall of the tubing, it is desirable the tubing is capable of delivering fluid in response to energy applied to the tubing by a medical infusion pump for a 24 hour period without more than 10% change in flow rate and more preferably without more than 5% change.

It is also desirable for pump compatible tubing to have an original cross-sectional diameter and to retain 95% of the original cross-sectional diameter after stretching the tubing with a 5 lb weight for 10 seconds.

C. Drip Chamber

The present invention further contemplates fabricating the drip chamber 40 shown in FIG. 6 from the primary polymers and blends described above in Sections I and II. The drip chamber can have a monolayer structure or a multiple layered structure. In a preferred form of the invention, the drip chamber is a monolayer structure of one of the blends of the present invention. The drip chamber 40 is preferably made in an injection molding process but can be made from other polymer processing techniques well known in the art without departing from the scope of the present invention.

D. Solvent Bonding

What is meant by the term "solvent bonding" is that one of the products made from one of the primary polymers or a blend described above can be exposed to a solvent to melt, dissolve or swell the product and then can be attached to another polymeric component to form a permanent bond.

Suitable solvents typically include those having a solubility parameter of less than about 20 $(MPa)^{1/2}$, more preferably less than about 19 $(MPa)^{1/2}$ and most preferably less than about 18 $(MPa)^{1/2}$ and include, but are not limited to, aliphatic hydrocarbons, aromatic hydrocarbons, mixtures of aliphatic hydrocarbons, mixtures of aromatic hydrocarbons and mixtures of aromatic and aliphatic hydrocarbons. Suitable aliphatic hydrocarbons include substituted and unsubstituted hexane, heptane, cyclohexane, cycloheptane, decalin, and the like. Suitable aromatic hydrocarbons include substituted and unsubstituted aromatic hydrocarbon solvents such as xylene, tetralin, toluene, and cumene. Suitable hydrocarbon substituents include aliphatic substituents having from 1–12 carbons and include propyl, ethyl, butyl, hexyl, tertiary butyl, isobutyl and combinations of the same. What is meant by the terms "aliphatic hydrocarbon" and "aromatic hydrocarbon" is a compound containing only carbon and hydrogen atoms. Suitable solvents will also have a molecular weight less than about 200 g/mole, more preferably less than about 180 g/mole and most preferably less than about 140 g/mole.

What is meant by a "rigid component" is a connector or other device commonly used in peritoneal dialysis or I.V. administration sets and typically having a modulus of elasticity of greater than about 30,000 psi. Suitable polymers for fabricating a rigid component includes homopolymers and copolymers of polypropylenes, polyesters, polyamides, polystyrenes, polyurethanes, polycarbonates, cylic olefin containing polymers and bridged polycyclic olefin containing polymers. Suitable cyclic olefin containing polymers and bridged polycylic olefin containing polymers are disclosed in U.S. patent application Ser. Nos. 09/393,912, 09/393,052, and 09/393,051 which are incorporated herein by reference and made a part hereof.

The present invention provides a method for assembling components of an infusion set into medical assemblies using solvent bonding techniques. Solvent bonding techniques can be used to join together separate articles made from the polybutadiene blends set forth above in Sections I and II. An example would be joining a polybutadiene blend tubing to a polybutadiene drip chamber.

The present invention further provides solvent bonding articles made from the primary polymers and blends set forth above in Sections I and II with COC containing polymers and polymer blends. The COC containing polymers can be pure COC or blends of COC resins with other COC resins. Suitable COC containing polymer blends include any blends of COC with polybutadienes notwithstanding the relative amounts by weight of COC and polybutadiene in the blend. Other suitable COC blends, such as COC/ULDPE blends will preferably have at least about 30% by weight of COC and more preferably more than about 50% COC by weight of the blend.

The method of solvent bonding includes the steps of: (1) providing a first article of a polymer or polymer blend described above in Sections I and II; (2) providing a second article of a material selected from the group comprising: (a) polybutadiene and polybutadiene containing blends described above in Sections I and II, (b) COC/polybutadiene blends, and (c) COC/other polymer blends where the COC is present in an amount by weight of at least about 30% by weight of the blend; (3) applying a solvent to one of the first article or the second article to define an interface area; and (4) bonding the first article to the second article along the interface area.

Suitable solvents are those having a solubility parameter of less than about 20 $(MPa)^{1/2}$, more preferably less than about 19 $(MPa)^{1/2}$ and most preferably less than about 18 $(MPa)^{1/2}$ and include, but are not limited to, aliphatic hydrocarbons, aromatic hydrocarbons, mixtures of aliphatic hydrocarbons, mixtures of aromatic hydrocarbons and mixtures of aromatic and aliphatic hydrocarbons. Suitable aliphatic hydrocarbons include substituted and unsubstituted hexane, heptane, cyclohexane, cycloheptane, decalin, and the like. Suitable aromatic hydrocarbons include substituted and unsubstituted aromatic hydrocarbon solvents such as xylene, tetralin, toluene, and cumene. Suitable hydrocarbon substituents include aliphatic substituents having from 1–12 carbons and include propyl, ethyl, butyl, hexyl, tertiary butyl, isobutyl and combinations of the same. What is meant by the terms "aliphatic hydrocarbon" and "aromatic hydrocarbon" is a compound containing only carbon and hydrogen atoms. Suitable solvents will also have a molecular weight less than about 200 g/mole, more preferably less than about 180 g/mole and most preferably less than about 140 g/mole.

It may also be desirable to improve solvent bonding to provide a tubing having a textured, frosted or otherwise roughened outer surface in the area where the tubing will be bonded (the interface area) or along the entirety of the tubing outer surface.

The following are non-limiting examples of the present invention and should not be used to limit the scope of the claims set forth below.

EXAMPLES

Example-1

Pump Accuracy

Pump tubings made from JSR B810, JSR RB820, and blends from these two materials were extruder using a single screw extruder. The pump flow rate accuracy test was done using a Baxter Flo-Gard 6201 mechanical pump and a Colleague mechanical pump. The percent of changes of cumulative flow rate from the 1st hour to the 24th hours were listed in Table-1.

TABLE 1

| Material Type | Formulation RB810/RB820 | Pump Type | % change 1 to 24 hours |
|---|---|---|---|
| PVC/ PL1847 | — | Flo-Gard 6201 | −2.90% |
| Polybutadiene | 100/0 | Flo-Gard 6201 | −2.63% |
| Polybutadiene | 70/30 | Flo-Gard 6201 | −2.98% |
| Polybutadiene | 60/40 | Flo-Gard 6201 | −3.11% |
| PVC/ PL1847 | — | Colleague | −0.40% |
| Polybutadiene | 100/0 | Colleague | −1.42% |
| Polybutadiene | 70/30 | Colleague | −1.15% |
| Polybutadiene | 60/40 | Colleague | 0.73% |

Example-2

Effect of Aging on the Stiffness of Polybutadiene Tubing

Tubing made of JSR RB820 polybutadiene was extruded and tested for tensile modulus at 20 in/min speed over a period of 50 days. The tensile modulus was listed in Table-2.

TABLE 2

Tensile modulus of RB820 tubing measure at various days after the tubing extrusion.

| Time (days) | Modulus (psi) |
|---|---|
| 3 | 2900 |
| 15 | 3200 |
| 21 | 4100 |
| 23 | 4400 |
| 31 | 4900 |
| 43 | 4950 |
| 55 | 5000 |

Example-3

Effect of Heat Treatment on Tubing Stiffness

RB820 tubings aged at ambient condition after extrusion for 2 to 23 days were then heat treated at 80 C for 10 minutes to 60 minutes, and then aged at ambient condition for up to 46 days. It was found that the tubing modulus will reduce to a consistent lower level than the initially higher and different moduli, and stayed stable after the heat treatment. Table-3 lists the tubing modulus as function of time of aging after extrusion but before heat treatment, time of heat treatment at 80 C, and time of aging after heat treatment.

TABLE 3

| T1 (days) | T2 (minutes) | T3 (days) | Modulus (psi) |
|---|---|---|---|
| 2 | 60 | 2 | 1850 |
| 10 | 60 | 4 | 2130 |
| 10 | 60 | 46 | 2270 |
| 23 | 10 | 1 | 2090 |
| 23 | 30 | 1 | 2100 |
| 23 | 30 | 9 | 2160 |
| 23 | 30 | 35 | 2210 |

T1: Aging time at ambient after extrusion but before heat treatment
T2: Time of heat treatment at 80 degree C.
T3: Aging time after heat treatment

Example-4

Effect of Heat Treatment on Tubing Stiffness

Tubing made from a 50/50 blend of RB810 and RB820 was extruded and aged at ambient condition for about 6 months and then heat treated at 60 C, 70 C and 80 C for 10 minutes to 120 minutes, and then aged at ambient condition for up to 22 days. It was found that the modulus of the tubing was also reduced to a consistently lower value than the initially higher modulus, and stayed stable after the heat treatment. Table-4 lists the tubing modulus as function of heat treatment temperature, heat treatment time, and aging time after the heat treatment.

TABLE 4

| Temperature (° C.) | T2 (minutes) | T3 (days) | Modulus (psi) |
|---|---|---|---|
| Control (No heat treatment) | | | 2200 |
| 60 | 60 | 1 | 1110 |
| 60 | 120 | 4 | 1220 |
| 60 | 120 | 12 | 1230 |
| 60 | 120 | 22 | 1230 |
| 70 | 10 | 4 | 1170 |
| 70 | 10 | 12 | 1150 |
| 70 | 10 | 22 | 1200 |
| 70 | 30 | 4 | 1150 |
| 80 | 10 | 4 | 1200 |
| 80 | 30 | 4 | 1270 |
| 80 | 30 | 12 | 1250 |
| 80 | 30 | 22 | 1240 |

T2: Time of heat treatment
T3: Aging time after heat treatment

Example-5

Effect of Heat Treatment on Stiffness of Radiation Sterilized Polybutadiene Tubing Tubing made from a 50/50 blend of RB810 and RB820 was extruded and aged at ambient condition for about 6 months, Gamma sterilized at about 25 kGy, and heat treated at 60 C, 70 C and 80 C for 10 minutes to 120 minutes, and then aged at ambient condition for up to 22 days. It was found that the tensile modulus of the tubing was also reduced to a value consistently lower than the initially higher modulus, and stayed stable after the heat treatment. Table-5 lists the tubing modulus as function of heat treatment temperature, heat treatment time, and aging time after the heat treatment.

TABLE 5

| Temperature (° C.) | T2 (minutes) | T3 (days) | Modulus (psi) |
|---|---|---|---|
| Control (No heat treatment) | | | 2336 |
| 60 | 60 | 4 | 1530 |
| 60 | 120 | 4 | 1530 |
| 60 | 120 | 12 | 1520 |
| 60 | 120 | 22 | 1600 |
| 70 | 10 | 4 | 1430 |
| 70 | 10 | 12 | 1450 |
| 70 | 10 | 22 | 1470 |
| 70 | 30 | 4 | 1450 |
| 80 | 10 | 4 | 1460 |
| 80 | 30 | 4 | 1400 |
| 80 | 30 | 12 | 1480 |
| 80 | 30 | 22 | 1540 |

T2: Time of heat treatment
T3: Aging time after heat treatment

Example-6

Effect of Heat Treatment on Tensile Curve of 1,2 polybutadiene

Figure 7:
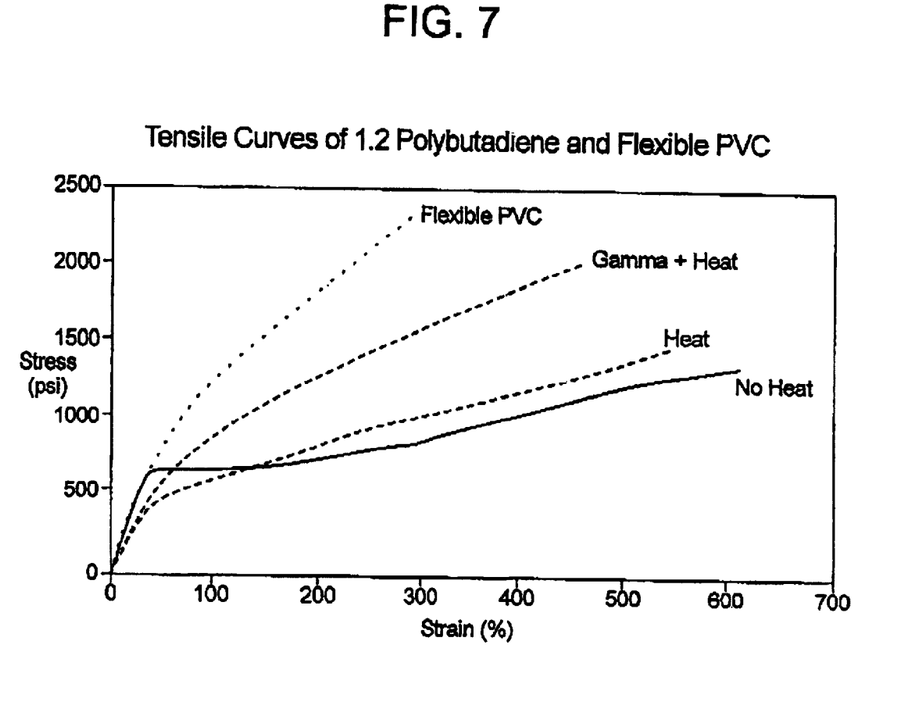
FIG. 7 shows tensile curves for 1,2-polybutadiene and flexible PVC tubing.

Tubing made from a 50/50 blend of RB810 and RB820 1,2 polybutadienes from Example-5 was tensile tested and compared with flexible medical PVC tubing. FIG. 7 shows the curves of the a flexible PVC tubing, the polybutadiene tubing with and without heat treatment at 70 C for 10 minutes, and polybutadiene tubing with both radiation sterilization and heat treatment. FIG. 7 shows that heat treatment can remove the distinct yield phenomena as shown as the kink point from the stress-strain tensile curve, and makes the material more like flexible PVC tubing. The heat treatment also further shift the stress-strain curve of radiation sterilized polybutadiene closer to the shape of flexible PVC tubing. These changes will make the polybutadiene tubing have less tendency to kink and more elastic which make it more suitable for usage in pump tubing application.

Example-7

Solvent Bonding of Polybutadiene to Cyclic-Olefin Copolymer

Tubing made from RB810 and RB820 were solvent bonded to an Y-site which was injection molded from a cyclic olefin copolymer, Grade name Topas 8007, made by Ticona. The polybutadiene tubing has an outside diameter of about 0.14 inches and a wall thickness of about 0.019 inches. The outside diameter of the tubing was to be solvent bonded to the inside diameter of the y-site component. The solvent used for the bonding was Decalin, available from the Aldrich Chemicals Co. Table-6 summarizes the solvent bond strength results of polybutadiene tubing to the y-site made of cyclic-olefin copolymer. The bond strength is strong. Roughening the tubing surface further enhances the bond strength.

TABLE 6

| Formulation RB810/RB820 | Tubing surface | Solvent bond strength (lb force) |
| --- | --- | --- |
| 100/0 | smooth | 7.95 |
| 60/40 | smooth | 7.5 |
| 60/40 | rough | 10.8 |
| 50/50 | smooth | 8.4 |
| 50/50 | rough | 11.2 |
| 0/100 | smooth | 10.4 |

Example-8

Solvent Bonding of Polybutadiene to Cyclic-Olefin Copolymer

Tubing made from RB810 and RB820 were solvent bonded to an Y-site which was injection molded from a cyclic olefin copolymer, Grade name Topas 8007, made by Ticona. The polybutadiene tubing has an outside diameter of about 0.14 inches and a wall thickness of about 0.019 inches. The outside diameter of the tubing was to be solvent bonded to the inside diameter of the y-site component. The solvent used for the bonding was Cyclohexane, Decalin, or Tetralin, all available from the Aldrich Chemicals Co. Table-7 summarizes the solvent bond results of polybutadiene tubing to the cyclic-olefin copolymer y-site. All these solvents were able to bond polybutadiene to cyclic-olefin copolymer well.

TABLE 7

| Formulation RB810/RB820 | Solvent | Solvent bond strength (lb force) |
| --- | --- | --- |
| 20/80 | cyclohexane | 5.5 |
| 20/80 | decalin | 7.7 |
| 20/80 | tetralin | 7.2 |
| 30/70 | cyclohexane | 7.4 |
| 30/70 | decalin | 10.1 |
| 30/70 | tetralin | 10.7 |
| 60/40 | cyclohexane | 6.8 |
| 60/40 | decalin | 11 |
| 60/40 | tetralin | 8.2 |

While specific embodiments have been illustrated and described, numerous modifications are possible without departing from the spirit of the invention, and the scope of protection is only limited by the scope of the accompanying claims.

What is claimed is:

1. A polymer blend for fabricating medical products comprising:
   a first low crystallinity syndiotactic 1,2 polybutadiene present from about 1% to about 99% by weight of the blend and having a first melting point temperature; and
   a second syndiotactic 1,2 polybutadiene present from about 1% to 99% by weight of the blend and having a melting point temperature higher than the first melting point temperature.

2. The blend of claim 1 wherein the first melting point temperature is less than about 100° C.

3. The blend of claim 1 wherein the first melting point temperature is less than about 90° C.

4. The blend of claim 1 wherein the second syndiotactic 1,2 polybutadiene is a low crystallinity syndiotactic 1,2 polybutadiene.

5. The blend of claim 1 further comprising an effective amount of a hindered amine.

6. An irradiated polymer blend for fabricating medical products, comprising:
   a first 1,2 polybutadiene present from about 1% to about 99% by weight of the blend and having a first melting point temperature;
   a second 1,2 polybutadiene present from about 1% to about 99% by weight of the blend and having a second melting point temperature higher than the first melting point temperature; and
   the blend having a gel content of at least 20%.

7. The blend of claim 6 wherein the first melting point temperature is less than about 100° C.

8. The blend of claim 6 wherein the first melting point temperature is less than about 90° C.

9. The blend of claim 6 wherein the first 1,2 polybutadiene is a first syndiotactic 1,2 polybutadiene.

10. The blend of claim 9 wherein the first syndiotactic 1,2 polybutadiene is a low crystallinity syndiotactic 1,2 polybutadiene.

11. The blend of claim 9 wherein the second 1,2 polybutadiene is a second syndiotactic 1,2 polybutadiene.

12. The blend of claim 11 wherein the second syndiotactic 1,2 polybutadiene is a second low crystallinity syndiotactic 1,2 polybutadiene.

13. The blend of claim 6 further comprising an effective amount of a hindered amine.

14. A tubing comprising:
   a sidewall of a polymer blend comprising a first 1,2 polybutadiene present from about 1% to about 99% by weight of the blend and having a first melting point temperature, and a second 1,2 polybutadiene present from about 1% to about 99% by weight of the blend and having a second melting point temperature higher than the first melting point temperature.

15. The tubing of claim 14 wherein the first melting point temperature is less than about 100° C.

16. The tubing of claim 14 wherein the first melting point temperature is less than about 90° C.

17. The tubing of claim 14 wherein the first 1,2 polybutadiene is a first syndiotactic 1,2 polybutadiene.

18. The tubing of claim 17 wherein the first syndiotactic 1,2 polybutadiene is a low crystallinity syndiotactic 1,2 polybutadiene.

19. The tubing of claim 17 wherein the second 1,2 polybutadiene is a second syndiotactic 1,2 polybutadiene.

20. The tubing of claim 19 wherein the second syndiotactic 1,2 polybutadiene is a second low crystallinity syndiotactic 1,2 polybutadiene.

21. The tubing of claim 14 further comprising an effective amount of a hindered amine.

22. A tubing comprising:
a sidewall of a polymer blend comprising a first 1,2 polybutadiene present from about 1% to about 99% by weight of the blend and having a first melting point temperature, a second 1,2 polybutadiene present from about 1% to about 99% by weight of the blend and having a second melting point temperature higher than the first melting point temperature; and
the tubing having been exposed to sterilizing radiation from about 15 kGys to about 45 kGys.

23. The tubing of claim 22 wherein the first melting point temperature is less than about 100° C.

24. The tubing of claim 22 wherein the first melting point temperature is less than about 90° C.

25. The tubing of claim 22 wherein the first 1,2 polybutadiene is a first syndiotactic 1,2 polybutadiene.

26. The tubing of claim 25 wherein the first syndiotactic 1,2 polybutadiene is a low crystallinity syndiotactic 1,2 polybutadiene.

27. The tubing of claim 25 wherein the second 1,2 polybutadiene is a second syndiotactic 1,2 polybutadiene.

28. The tubing of claim 27 wherein the second syndiotactic 1,2 polybutadiene is a second low crystallinity syndiotactic 1,2 polybutadiene.

29. The tubing of claim 22 further comprising an effective amount of a hindered amine.

30. A tubing comprising:
a first 1,2 polybutadiene present from about 1% to about 99% by weight of the blend and having a first melting point temperature;
a second 1,2 polybutadiene present from about 1% to about 99% by weight of the blend and having a second melting point temperature higher than the first melting point temperature;
the tubing having been exposed to sterilizing radiation from about 15 kGys to about 45 kGys; and
wherein the tubing is capable of delivering fluid in response to energy applied to the tubing by a medical infusion pump for a 24 hour period without generating visible particulate matter.

31. The tubing of claim 30 wherein the tubing has an original cross-sectional diameter and retains 95% of the original cross-sectional diameter after stretching the tubing with a 5 lb weight for 10 seconds.

32. A multiple layered tubing comprising:
a first layer of a polymer blend comprising a first 1,2 polybutadiene present from about 1% to about 99% by weight of the blend and having a first melting point temperature, and a second 1,2 polybutadiene present from about 1% to about 99% by weight of the blend and having a second melting point temperature higher than the first melting point temperature; and
a second layer of a polymeric material attached to the first layer and concentrically disposed with respect thereto.

33. The tubing of claim 32 wherein the second layer is a polyolefin.

34. The tubing of claims 33 wherein the polyolefin is obtained from a polymerizing an olefin.

35. The tubing of claim 34 wherein the olefin is selected from the group consisting of cyclic olefins, and acyclic olefins.

36. The tubing of claim 34 wherein the polyolefin is a 1,2 polybutadiene.

37. The tubing of claim 34 wherein the polyolefin is a syndiotactic 1,2 polybutadiene.

38. The tubing of claim 34 wherein the polyolefin is a low crystallinity syndiotactic 1,2 polybutadiene.

39. The tubing of claim 38 wherein the second layer is concentrically positioned about the first layer.

40. The tubing of claim 38 wherein the second layer is concentrically positioned inside the first layer.

41. The tubing of claim 40 wherein the low crystallinity syndiotactic 1,2 polybutadiene has a crystallinity less 50%.

42. The tubing of claim 40 wherein the low crystallinity syndiotactic 1,2 polybutadiene has a crystallinity less than about 45%.

43. The tubing of claim 40 wherein the low crystallinity syndiotactic 1,2 polybutadiene has a crystallinity of less than about 40%.

44. The tubing of claim 40 wherein the low crystallinity syndiotactic 1,2 polybutadiene has a crystallinity of from about 13% to about 40%.

45. The tubing of claim 40 wherein the low crystallinity syndiotactic 1,2 polybutadiene has a crystallinity of from about 15% to about 30%.

46. The tubing of claim 40 wherein the low crystallinity syndiotactic 1,2 polybutadiene has a melting point temperature of less than about 90° C.

47. The tubing of claim 40 wherein the low crystallinity syndiotactic 1,2 polybutadiene has a melting point temperature of higher than about 91° C. but less than 120° C.

48. A multiple layered tubing comprising:
a first layer of a polymer blend of a first low crystallinity syndiotactic 1,2 polybutadiene having a first melting point temperature lower than about 90° C. and present from about 1% to about 99% by weight of the blend and a second low crystallinity syndiotactic 1,2 polybutadiene having a second melting point temperature higher than about 91° C. and present from about 1% to about 99% by weight of the blend; and
a second layer of a polymeric material attached to the first layer and concentrically disposed with respect thereto.

49. The tubing of claim 48 wherein the second layer is a polyolefin.

50. The tubing of claim 49 wherein the polyolefin is obtained from polymerizing an olefin.

51. The tubing of claim 50 wherein the olefin is selected from the group consisting of cyclic olefins and acyclic olefins.

52. The tubing of claim 50 wherein the polyolefin is a 1,2 polybutadiene.

53. The tubing of claim 52 wherein the 1,2 polybutadiene is a syndiotactic 1,2 polybutadiene.

54. The tubing of claim 52 wherein the 1,2 polybutadiene is a low crystallinity syndiotactic 1,2 polybutadiene.

55. The tubing of claim 54 wherein the second layer is concentrically positioned about the first layer.

56. The tubing of claim 54 wherein the second layer is concentrically positioned inside the first layer.

57. The tubing of claim 54 wherein the low crystallinity syndiotactic 1,2 polybutadiene has a crystallinity less 50%.

58. The tubing of claim 54 wherein the low crystallinity syndiotactic 1,2 polybutadiene has a crystallinity less than about 45%.

59. The tubing of claim 54 wherein the low crystallinity syndiotactic 1,2 polybutadiene has a crystallinity of less than about 40%.

60. The tubing of claim 54 wherein the low crystallinity syndiotactic 1,2 polybutadiene has a crystallinity of from about 13% to about 40%.

61. The tubing of claim 54 wherein the low crystallinity syndiotactic 1,2 polybutadiene has a crystallinity of from about 15% to about 30%.

62. The tubing of claim 54 wherein the low crystallinity syndiotactic 1,2 polybutadiene has a melting point temperature of less than about 90° C.

63. The tubing of claim 54 wherein the low crystallinity syndiotactic 1,2 polybutadiene has a melting point temperature of higher than about 91° C. but less than 120° C.

64. A multiple layered tubing comprising:
a first layer of a polymer blend comprising a first 1,2 polybutadiene present from about 1% to about 99% by weight of the blend and having a first melting point temperature, and a second 1,2 polybutadiene present from about 1% to about 99% by weight of the blend and having a second melting point temperature higher than the first melting point temperature;
a second layer of a polymeric material attached to the first layer and concentrically disposed with respect thereto; and
wherein the tubing having been exposed to sterilizing radiation from about 15 kGys to about 45 kGys.

65. A multiple layered tubing comprising:
a first layer of a polymer blend of a first low crystallinity syndiotactic 1,2 polybutadiene having a first melting point temperature less than about 90° C. and present from about 1% to about 99% by weight of the blend and a second low crystallinity syndiotactic 1,2 polybutadiene having a second melting point temperature higher than about 91° C. and present from about 1% to about 99% by weight of the blend;
a second layer of a polymeric material attached to the first layer and concentrically disposed with respect thereto; and
wherein the tubing having been exposed to sterilizing radiation from about 15 kGys to about 45 kGys.

66. The tubing of claim 65 wherein the second layer is a polyolefin.

67. The tubing of claims 66 wherein the polyolefin is obtained from polymerizing an olefin.

68. The tubing of claim 67 wherein the olefin is selected from the group of cyclic olefins and acyclic olefins.

69. The tubing of claim 66 wherein the polyolefin is a syndiotactic 1,2 polybutadiene.

70. The tubing of claim 66 wherein the polyolefin is a third low crystallinity syndiotactic 1,2 polybutadiene.

71. The tubing of claim 70 wherein the third low crystallinity syndiotactic 1,2 polybutadiene has a crystallinity less than 50%.

72. The tubing of claim 70 wherein the third low crystallinity syndiotactic 1,2 polybutadiene has a crystallinity less than about 45%.

73. The tubing of claim 70 wherein the third low crystallinity syndiotactic 1,2 polybutadiene has a crystallinity of less than about 40%.

74. The tubing of claim 70 wherein the third low crystallinity syndiotactic 1,2 polybutadiene has a crystallinity of from about 13% to about 40%.

75. The tubing of claim 70 wherein the third low crystallinity syndiotactic 1,2 polybutadiene has a crystallinity of from about 15% to about 30%.

76. The tubing of claim 70 wherein the third low crystallinity syndiotactic 1,2 polybutadiene has a melting point temperature of less than about 90° C.

77. The tubing of claim 70 wherein the third low crystallinity syndiotactic 1,2 polybutadiene has a melting point temperature of higher than about 91° C. but less than about 120° C.

78. A multiple layered tubing for an infusion pump comprising:
a first layer of a first polymer blend of a first low crystallinity syndiotactic 1,2 polybutadiene having a first melting point temperature less than about 90° C. and present from about 1% to about 99% by weight of the first blend and a second low crystallinity syndiotactic 1,2 polybutadiene having a second melting point temperature higher than about 91° C. and present from about 1% to about 99% by weight of the first blend;
a second layer of a polymeric material concentrically disposed within the first layer and attached thereto and being of a second polymer blend comprising a third low crystallinity syndiotactic 1,2 polybutadiene present from about 1% to about 99% by weight of the second blend and having a third melting point temperature, and a fourth 1,2 polybutadiene present from about 1% to about 99% by weight of the second blend and having a fourth melting point temperature higher than the third melting point temperature; and
wherein the tubing having been exposed to sterilizing radiation from about 15 kGys to about 45 kGys.

79. The tubing of claim 78 wherein the tubing has an original cross-sectional diameter and retains 95% of the original cross-sectional diameter after stretching the tubing with a 5 lb weight for 10 seconds.

80. The tubing of claim 79 wherein the third melting point temperature is less than about 90° C.

81. A method for fabricating a tubing comprising the steps of:
providing a blend of a first 1,2 polybutadiene present from about 1% to about 99% by weight of the blend and having a first melting point temperature and a second 1,2 polybutadiene present from about 1% to about 99% by weight of the blend and having a second melting point temperature higher than the first melting point temperature;
extruding the blend into a tubing; and
heating the tubing to reduce the tendency of the tubing to crystallize over time.

82. A polymer blend for fabricating medical products comprising:
a first 1,2 polybutadiene present from about 1% to about 99% by weight of the blend and having a first melting point temperature; and
a second 1,2 polybutadiene present from about 1% to about 99% by weight of the blend and having a second melting point temperature different than the first melting point temperature wherein the first and second 1,2 polybutadienes are crosslinked.

83. The blend of claim 82 wherein the first 1,2 polybutadiene is syndiotactic.

84. The blend of claim 82 wherein the first 1,2 polybutadiene is a low crystallinity syndiotactic 1,2 polybutadiene.

85. The blend of claim 82 wherein the first and the second 1,2 polybutadiene are each a low crystallinity syndiotactic 1,2 polybutadiene.

* * * * *

UNITED STATES PATENT AND TRADEMARK OFFICE
CERTIFICATE OF CORRECTION

| | |
|---|---|
| PATENT NO. | : 7,011,872 B2 |
| APPLICATION NO. | : 09/939294 |
| DATED | : March 14, 2006 |
| INVENTOR(S) | : Ding et al. |

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by 258 days Delete the phrase "by 258 days" and insert -- by 378 days--

Signed and Sealed this

Twenty-eighth Day of November, 2006

JON W. DUDAS
*Director of the United States Patent and Trademark Office*